United States Patent [19]

Carroll et al.

[11] Patent Number: 5,246,005
[45] Date of Patent: Sep. 21, 1993

[54] APPARATUS AND METHOD FOR PRODUCING STATISTICALLY VALID DISCRIMINABLE SIGNALS

[75] Inventors: Robert G. Carroll, Largo, Fla.; Robin A. Wise, Jr., Morgan Hill, Calif.

[73] Assignee: Care Wise Medical Products Corporation, Morgan Hill, Calif.

[21] Appl. No.: 724,685

[22] Filed: Jul. 2, 1991

[51] Int. Cl.⁵ .............................................. A61B 6/12
[52] U.S. Cl. .................................... 128/654; 128/659
[58] Field of Search ............ 128/687, 688, 689, 690, 128/654, 659, 653.1; 250/388

[56] References Cited

U.S. PATENT DOCUMENTS

| | | | |
|---|---|---|---|
| 3,978,849 | 9/1989 | Geneen | 128/690 |
| 4,654,528 | 3/1987 | Cloud, Jr. et al. | 250/388 |
| 4,867,442 | 9/1989 | Matthews | 128/689 |
| 4,889,991 | 12/1989 | Ramsey et al. | 128/659 |
| 4,959,547 | 9/1990 | Carroll et al. | 250/336.1 |
| 5,042,504 | 8/1991 | Huberti | 128/779 |

FOREIGN PATENT DOCUMENTS 2158572 12/1985 United Kingdom ................ 250/388
2166246 4/1986 United Kingdom ................ 128/689

Primary Examiner—Lee S. Cohen
Assistant Examiner—Samuel Gilbert
Attorney, Agent, or Firm—Caesar, Rivise, Bernstein, Cohen & Pokotilow, Ltd.

[57] ABSTRACT

An apparatus and method for producing audible signals, which are representative of the level of detected radiation from a probe, and which are statistically valid. The output of a radiation detector is a series of pulses, which are counted for a predetermined amount of time. At least two count ranges are defined by circuitry in the apparatus and the count range which includes the input count is determined. For each count range, an audible signal is produced which is audibly discriminable from the audible signal produced for every other count range. The mean values of each count range are chosen to be statistically different, e.g., 1, 2, or 3 standard deviations, from the mean of adjacent lower or higher count ranges. The parameters of the audible signal, such as frequency, voice, repetition rate, and/or intensity are changed for each count range to provide a signal which is discriminable from the signals of any other count range.

57 Claims, 2 Drawing Sheets

APPARATUS AND METHOD FOR PRODUCING STATISTICALLY VALID DISCRIMINABLE SIGNALS

BACKGROUND OF THE INVENTION

This invention relates generally to the detection of radiation and more particularly to signal discrimination used with probes for the detecting of radiation in the cells of biological systems.

In the detection and/or treatment of certain diseases, e.g., cancer, radiopharmaceuticals such as monoclonal antibodies tagged with radioactive isotopes (e.g., Iodine 125, Indium 111, Technetium 99m, etc.) are frequently injected into the body of the patient. These isotope-tagged antibodies tend to seek out particular tissues, e.g., the cancerous tissue. Gamma-ray detectors are then employed to detect the gamma-ray radiation emitted by the tagged antibodies to localize and/or provide an image of the radiation emitting tissue(s).

In order to expedite the localization of the tagged tissue, surgeons are increasingly turning to the use of hand-held radiation detecting probes. One such probe is commercially available from Care Wise Medical Products, Inc. of Morgan Hill, Calif. 95037, the assignee of this application, under the trademark ONCOPROBE. That probe is electrically connected to an analyzer/monitor.

The output of the ONCOPROBE device probe is a series of electrical pulses having a count or repetition rate, which is related to the counts per seconds of gamma-ray radiation received by it. The higher the electrical pulse rate, the greater the counts per seconds of received radiation. The electrical pulses are used by the analyzer to provide an audible output signal representative of the counts.

In U.S. Pat. No. 4,959,547, also assigned to the same assignee as this invention, there is disclosed a probe with an adjustment mechanism (i.e., collimator) for adjusting the solid angle through which the radiation may pass to the radiation detector, e.g., a crystal, within the probe's body. The collimating probe assists the surgeon by enabling him or her to reduce the angle through which radiation reaches the detector to localize smaller radiation sources or "hot spots" in a noise background.

A problem with the use of monoclonal antibodies tagged with radioactive isotopes to detect cancerous tumors is that the radioactivity tends to diffuse throughout the body and also concentrate particularly around certain organs and other parts of the body. Thus, approximately 35% of the injected radioactive isotope is absorbed in the liver, 20% is absorbed in the blood pool, and most of the remainder is diffused generally throughout the body. Only about 0.5% of the total available radiation is absorbed by, and is concentrated in, cancerous tumors. This results in a extremely high background level of radiation as compared to the available target signal. This is particularly true near the liver and other organs which have high concentrations of radiation, which makes the detection of cancer cells difficult.

The situation is further exacerbated by the fact that the background radiation is variable and uneven ("lumpy"), and can change rapidly as the probe is moved about by the surgeon.

During the localization procedure, the surgeon is guided by the sound produced by the analyzer connected to the probe. In this regard, pulses from the gamma-ray detector in the probe provide signals to the analyzer to modulate an audio tone so that the surgeon hears an audible signal whose repetition rate is proportional to the counts per second of radiation detected by the probe. The higher the audible repetition rate, the greater the counts per second of radiation detected.

At present, the problem of high background radiation is attempted to be neutralized or obviated by operator control, i.e., the instrument's operator sets the count threshold levels to remove or "null out" counts representative of background radiation, so that the remaining detected radiation represents the hot spots which the surgeon seeks (i.e., the tagged tissue).

This method, while a step in the right direction, nevertheless leaves much to be desired. In this connection, with certain types of isotopes in common use, such as Iodine 125, which emits a 35 Ke V gamma in only 7% of its disintegrations resulting in low counts per second, a strong signal is about 20 counts per second, whereas the background radiation may be as high as 10 counts per second. Thus, when the background level, which is extremely variable, drops, radiation from hot spots is often not detected. Also, the setting of the threshold level is arbitrary and subject to error by the operator.

For systems which use Indium 111 and Technetium 99m, much higher radiation counts per second are available. Here, the gamma-ray detectors can produce repetition rates from 1 to 2 Hz up to 10,000 Hz. However, a problem with higher counts per second radiation levels is the sound discrimination ability of the human ear and brain. In this regard, human beings are able to discriminate between differences in repeating sounds very efficiently at low repetition rates, e.g., up to approximately 20 to 25 counts per second. However, humans are much less efficient at discriminating sounds at the higher repetition rates. Thus, the difference between a repetition rate of 5 versus 10 per second is easily discernable while the difference between a repetition rate of 120 to 150 is difficult for a human being to discern. Therefore, in addition to problems with strong and variable background radiation, even with target signals which are quite large, the ability of human beings to discriminate is poor at higher count rates.

An attempt to overcome this inherent limitation of humans by use of specialized techniques is disclosed in a report by Borgstrom et al. of the Division of Nuclear Medicine, Department of Radiology, University of Arizona entitled *Detection of Small Radiation Sources: The Effect of Mode of Count-Rate Presentation* (1989). That report was based on a study performed under a grant awarded by the National Cancer Institute, USPHS Grant No. C.A. 2347. Four methods were studied for the detection of small radiation sources. One method entailed the use of a rate meter to visually display the detected radiation rate. The second method entailed producing an audio signal (i.e., a "beep") at the detected repetition rate. The third method displayed the rate data on a cathode ray tube. The fourth method entailed use of a micro-processor to count and store the background radiation and to compare it to the incoming count rate. In accordance with that last method, the operator selected a threshold which is the background count plus an additional count set by the operator (a "delta"). If during the counting interval of ½ second duration taken at a suspected source site the count exceeds the background plus delta, a beeper is sounded until the end of the interval. As the count rate is increased, beeps become more frequent and have a longer duration.

It was found in the Borgstrom et al. study, that the fourth method, i.e., the method of utilizing the stored background count with the delta, was more efficient in detecting small radiation sources in the background than the other three modes of count-rate presentation. However, the fourth method of Borgstrom et al. still suffers from the fact that in practice, the radiation background levels encountered tend to be highly variable. Thus, if the background decreases in value, small radiation sources may be lost because the decreased value of the background plus the radiation source contribution are below the threshold setting plus the delta. Also the choice of the delta value is arbitrary and may not relate to a meaningful statistical variation in radiation.

Harris et al., in an article entitled *A CsI (Tl)-Crystal Surgical Scintillation Probe*, Nucleonics, November, 1956, disclose an operative probe with a sound system from a multi-vibrator with a range of 12 CPS to 1300 CPS. An eight position selection switch provides a variation in sensitivity in steps of about a factor of three. However, the system described in this article sets a threshold level for discrimination against background radiation.

Harvey and Lancaster, in a paper entitled *Technical and Clinical Characteristics of a Surgical Biopsy Probe*, The Journal of Nuclear Medicine, 22:184-186 (1981), disclose an audible count rate indicator that produces a signal proportional to a difference in counting rates. In this case the probe is first placed over representative normal tissue to set background level and a threshold is set, so that all subsequent audible rate beeps are an indication of count rates in excess of the background value.

The efficiency and effectiveness of hand-held radiation probes by surgeons in locating cancerous tumors have been progressively improved since their initial use. Initially, Iodine isotopes with low radiation counts per second and low frequencies were used. Then higher radiation energy and higher counts per second isotopes, such as Indium 111 and Technetium 99m, were introduced. The shielding of probes has been improved and collimating probes have been introduced to better discriminate and obtain the radiation from the target cells. Also, energy discrimination techniques are used to eliminate stray radiation. These improvements have resulted in increasing the probability of finding very small tumors, in the range of 8 mm-10 mm in diameter, to 90% or better. However, as discussed above, by setting arbitrary thresholds which eliminate background noise, or by automatically setting thresholds with arbitrary deltas, additional valuable data and information, which could further improve the chances of finding very small tumors in high background radiation, is lost.

Furthermore, with isotopes emitting higher counts per second, the count ranges of the detected radiation become higher and human beings are not able to properly discriminate statistical differences in count rates.

OBJECTS OF THE INVENTION

Accordingly, it is the general object of this instant invention to provide an apparatus and method for producing statistically valid discriminable signals which overcomes the shortcomings of the prior art.

It is a further object of this invention to provide an apparatus and method for producing statistically valid discriminable signals which allows the user to discern statistically meaningful changes in input signal parameters.

It is yet a further object of this invention to provide an apparatus and method for producing statistically valid discriminable signals which utilizes input background signals in conjunction with target signals to generate readily discriminable audible output signals.

It is still yet a further object of this invention to provide an apparatus and method for producing statistically valid discriminable signals by generating a series of audible output signals, each of which is discernably different for each statistically meaningful change in input signals.

It is another object of the invention to provide an apparatus and method for producing statistically valid discriminable signals which generates a series of audible output signals, wherein parameters of each signal are changed to make it readily discernably different from other signals.

It is yet another object of this invention to provide an apparatus and method for producing statistically valid discriminable signals, wherein the frequency, repetition rate duration, and/or intensity of audible output signals are changed to make them readily discernably different from each other.

It is still yet another object of this invention t provide an apparatus and method for producing statistically valid discriminable signals which samples radiation probe information and delays output signal generation for time periods which match the speed and movement of the probe by the user.

It is an additional object of the invention to provide an apparatus and method for producing statistically valid discriminable signals, wherein the range of input signals is divided into a set of ranges which are statistically different from each other and the output signals for each set are discernably different signals from other sets of ranges.

SUMMARY OF THE INVENTION

These and other objects of the instant invention are achieved by providing an apparatus and a method which provides the user of a radiation detection probe with a series of audible signals that are easily discernable from each other and which correspond to statistically valid differences in the input count being received from the radiation probe detector.

The range of input counts is divided into a set of count ranges having mean values that are statistically different from the means of the other count ranges. The values of the count ranges of frequencies are stored and a series of internal frequencies are generated, within the apparatus. The count range which includes the incoming frequency is determined, and for that count range, an output signal with a predetermined set of parameters, such as frequency, repetition rate, duration or intensity is generated to produce an audible signal. The respective output signal of each count range is discriminably different to the user from every other signal.

DESCRIPTION OF THE DRAWING

These and other objects of many of the intended features of this invention will become readily appreciated as the same becomes better understood by reference to the following detailed description when considered in connection with the accompanying drawing wherein.

DETAILED DESCRIPTION OF THE PREFERRED EMBODIMENT

Figure 1:
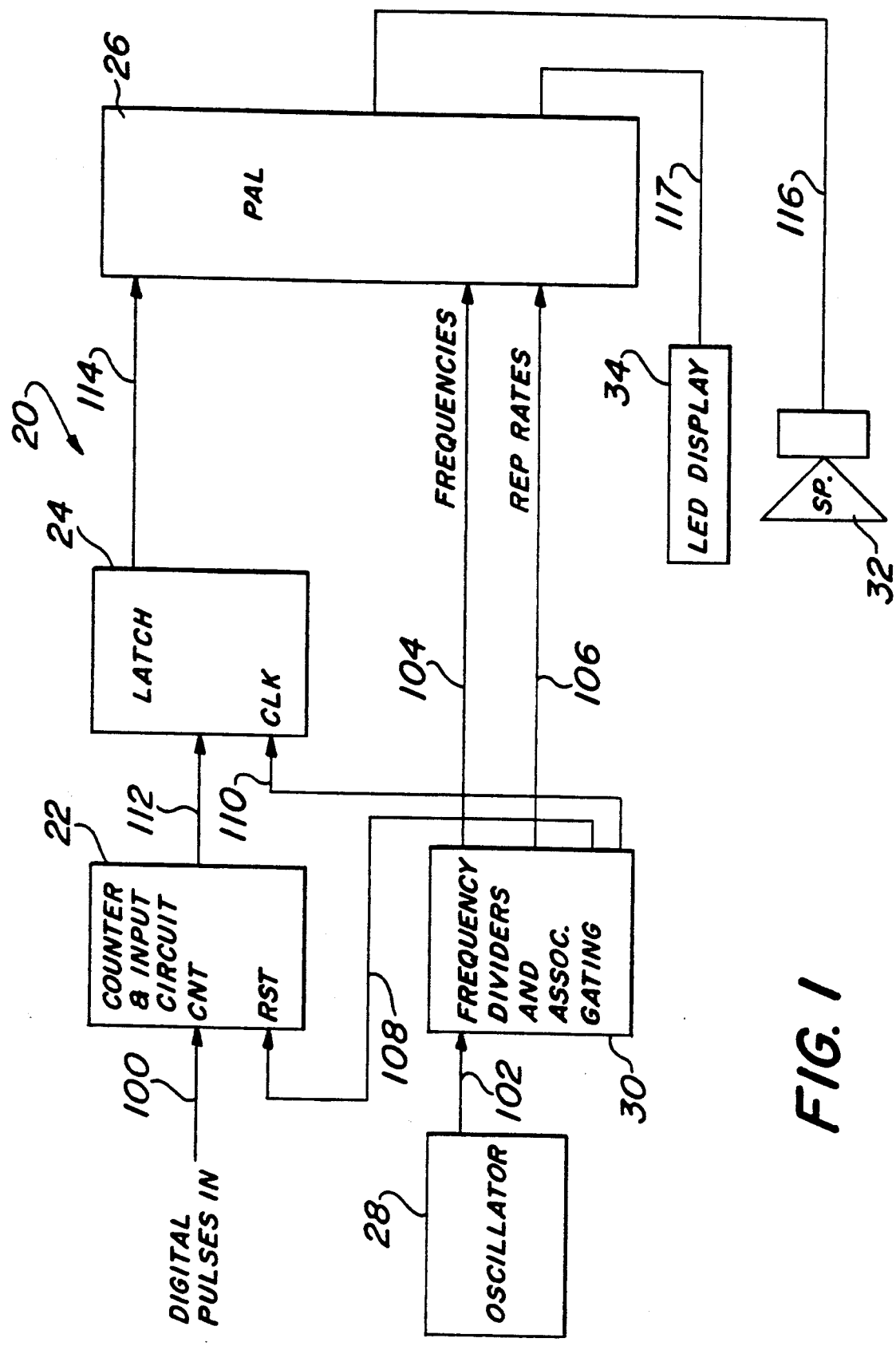
FIG. 1 is a block diagram of the apparatus of the instant invention.

Referring now in greater detail to the various figures of the drawing, wherein like reference characters refer to like parts, there is shown at 20 in FIG. 1 a block diagram of the circuitry of the apparatus of the instant invention. That circuitry may comprise an individual unit or may form a portion of an analyzer (not shown). In either case, the apparatus 20 basically comprises a counter and input circuit 22, a latch 24, a PAL (programmable array logic circuit) 26, an oscillator 28, frequency dividers and associated gating circuit 30, a speaker 32, and a visible LED display 34.

Digital count pulses from any small, hand held radiation probe (not shown), such as those prior art devices of the assignee of this invention, are provided to the "count input" or "CNT" of the counter and input circuit 22 via line 100. These pulses repeat at a frequency directly proportional to the counts per second of radiation detected by the probe.

In accordance with a preferred embodiment of this invention, the oscillator 28 is a one megahertz oscillator. The oscillator's output is connected to frequency dividers and associated gating circuit 30 by line 102. The frequency dividers circuit 30 is arranged to generate an array of frequencies and various repetition rates on lines 104 and on lines 106, respectively. These lines are connected to the PAL 26 and result in the generation of discernable audible output signals (as will be described later). In addition, the frequency divider circuit 30 also provides a signal, via line 108 to the reset (RST) of the counter circuit 22 and to the clock input ("CLK"), via line 110, to the latch 24.

The incoming digital pulses on line 100 are counted by the counter circuit 22 until a "reset" signal is received on line 108. This signal resets the counter circuit 22 for a new count. At the same time that the counter is cleared, the clock pulse on line 110 enables the latch 24 to accept the count from the counter circuit 22 and store it for transmission to the PAL 26, via lines 114.

The output of the PAL 26 establishes a series of tones or musical voices such as harp, organ, flute, etc. at various repetition rates. In this regard, the output of the PAL 26 is connected by line 116 to the speaker 32 which transduces the electrical output signals of the PAL 26 into audible tones or musical voices. Alternatively, or in conjunction with the speaker 32, an L.E.D. visual bar chart display 34, operated by electrical signals on lines 117, may be used.

The frequency divider circuit 30 also transmits digital signals of various frequencies and various repetition rates to the PAL 26 via lines 104 and lines 106 (as will be described in detail later). As used herein, the term repetition rate includes continuous tones which are considered to have a repetition rate approaching infinity.

The overall operation of the apparatus 20 will now be described. After the input pulses are counted for a predetermined time period (e.g., approximately 0.4 seconds for reasons to be described later) the output of the counter circuit 22, in digital form on lines 112, is latched and stored in the latch 24. Latch 24 transmits the stored count to the PAL 26 via lines 114. The total range of counts are divided into sets of ranges within the PAL 26, with each of the sets of ranges being divided further into sub-ranges. The PAL 26 is configured so that the mean of each sub-range is statistically different from its preceding or following sub-range. In accordance with this invention, the mean of each sub-range can be made to differ from adjacent sub-ranges by 1, 2, or 3 standard deviations. In fact, the means of each sub range may differ by any predetermined amount including a fraction of a standard deviation. The PAL 26 includes a look up table in which the sub-ranges are stored.

In operation, the PAL 26 determines in which sub-range the incoming count is included and generates a predetermined signal in response thereto. These signals, when provided to the speaker 32, or some other transducer, produce a tone or musical voice at a predetermined repetition rate. Thus, the apparatus 20, in effect, takes the total range of incoming signals (counts per second) and divides it into a series of individual count ranges to synthesize an audible output signal which corresponds to the incoming count.

The synthesized digital signals of the PAL 26 are chosen so that each succeeding change in the sub-range changes the character of the audible output signal to a frequency and/or repetition rate which is readily discernable by humans from any other frequency or repetition rate in the set of output signals. The following Table I is an exemplary set of audible output signals produced by the subject apparatus 20. In Table I, the term "SLOW" indicates a repetition rate of 8 cycles per second, the term "MEDIUM" indicates a repetition rate of 16 cycles per second, while the term "CONTINUOUS" means that the audible sound is continuous, that is, without interruption (i.e., a repetition rate approaching infinity). The count range frequencies and repetition rates shown in the Table I are exemplary and other suitable values or parameters may be chosen.

TABLE I

| COUNT RANGE/ SUB RANGE (GAMMA RAYS) FROM PROBE | REPETITION RATE OF AUDIBLE OUTPUT SIGNAL | FREQUENCY OF AUDIBLE OUTPUT SIGNAL |
| --- | --- | --- |
| 1-3 COUNTS | SLOW | 250 Hz |
| 4-7 COUNTS | MEDIUM | 250 Hz |
| 8-11 COUNTS | CONTINUOUS | 250 Hz |
| 12-15 COUNTS | SLOW | 500 Hz |
| 16-31 COUNTS | MEDIUM | 500 Hz |
| 32-47 COUNTS | CONTINUOUS | 500 Hz |
| 48-63 COUNTS | SLOW | 1K Hz |
| 64-79 COUNTS | MEDIUM | 1K Hz |
| 80-95 COUNTS | CONTINUOUS | 1K Hz |
| 96-127 COUNTS | SLOW | 2K Hz |
| 128-190 COUNTS | MEDIUM | 2K Hz |
| 191-255 COUNTS | CONTINUOUS | 2K Hz |
| 256-300 COUNTS | SLOW | 4K Hz |
| 301-349 COUNTS | MEDIUM | 4K Hz |
| 350-400 COUNTS | CONTINUOUS | 4K Hz |

Figure 2:
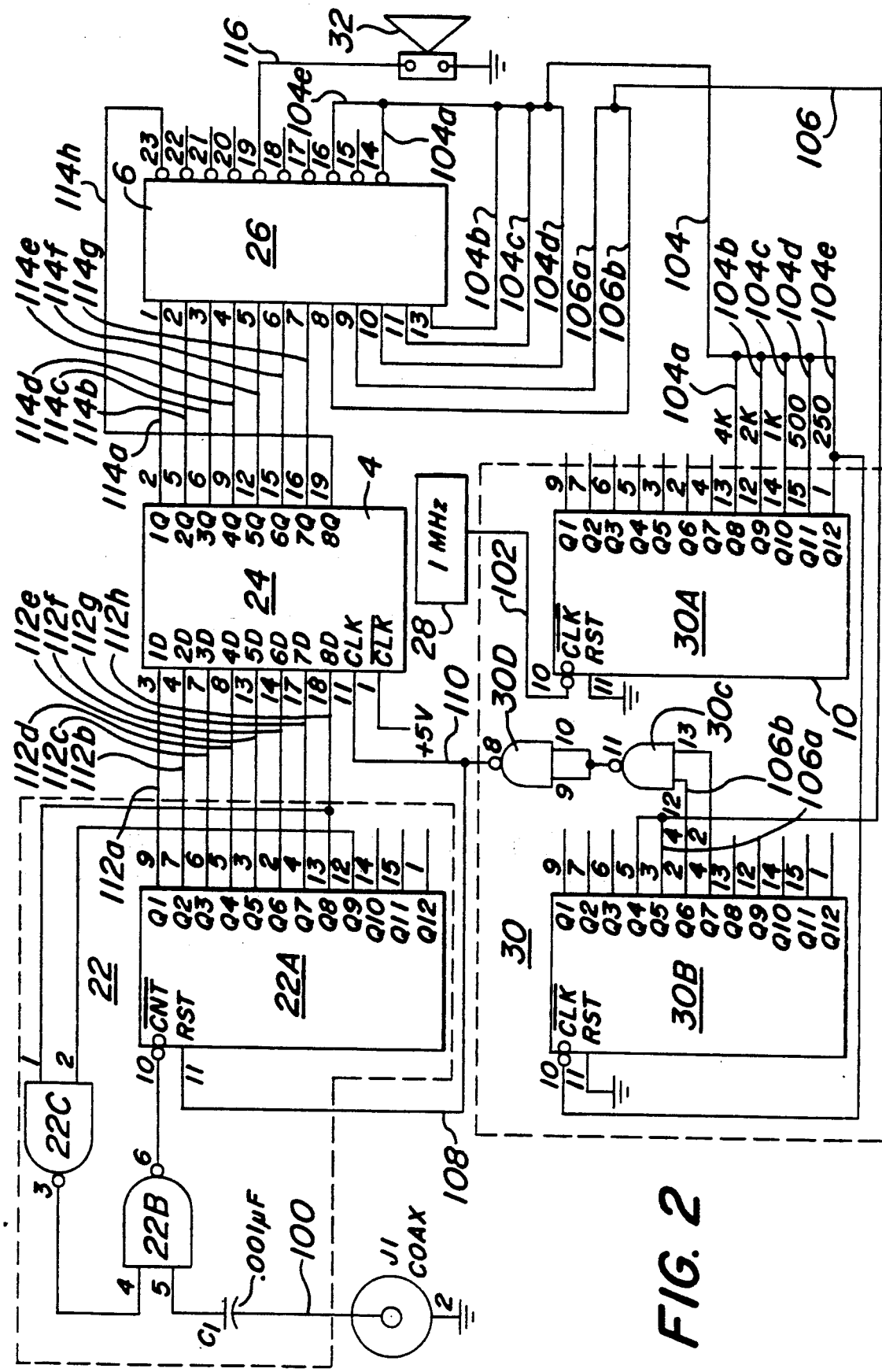
FIG. 2 is a detailed schematic of the apparatus of the instant invention.

Referring now to FIG. 2., the detailed operation of the apparatus 20 will now be described. It should be noted that the apparatus 20 may be assembled from standard off-the-shelf items. Exemplary part numbers and sources of these standard items are given below.

As can be seen in FIG. 2, the counter and input circuit 22 basically comprises a conventional integrated circuit counter 22A and two associated NAND gates, 22B and 22C. The input count from the radiation detection probe is provided via a coaxial cable, and associated jack J1 via line 100, to pin 5 of NAND gate 22B. A coupling capacitor C1 is located in line 100.

The NAND gate 22B enables the input count to appear at the "CNT" input of counter 22A, while NAND gate 22C disables NAND gate 22B and, therefore, cuts off the count input to prevent overflow of the counter 22A as described below. With the inputs at pins 4 and 5 of NAND gate 22B high, a negative count pulse appears at pin 10 of the counter 22A. Pin 4 of NAND gate 22B is connected to the output pin 3 of the NAND gate 22C. When the output of the NAND gate 22C goes low, NAND gate 22B is disabled cutting off the count to the counter 22A which prevents overflow of the count of stages one through eight of the counter. Therefore, the inputs to the NAND gate 22C at pins 1 and 2 are connected to the output of the eighth and ninth stages at pins 13 and 12, respectively, of the counter 22A. The input to counter 22A remains cut-off until the counter is reset, causing pin 3 of NAND gate 22C to go high, thereby enabling NAND GATE 22B and allowing the input pulses to again appear at pin 10 of counter 22A.

The NAND gates 22B and 22C and NAND gates 30C and 30D (to be described later), are provided by any standard quad, two-input NAND gate, e.g., a quad two-input NAND gate, having identification number 74/HCT00 sold by Signetics Co., National Semiconductor Corp., Texas Instruments and others.

The counter 22A is a standard 74/HCT4040 circuit, which is a twelve stage binary ripple counter also manufactured by Signetics Co., National Semiconductor Corp., Texas Instruments and others.

The oscillator 28 produces a one megahertz output signal to serve as the clock input to the frequency divider and associated gating circuit 30. That circuit basically comprises two divider circuits, 30A and 30B. Each circuit, 30A and 30B, is a conventional integrated circuit, e.g., a standard 74HCT4040. The circuits 30A and 30B are wired in tandem. The outputs of the frequency dividers 30A and 30B appear o lines 104 and lines 106. Pin 2 of the counter 30B carries a pulse which is approximately 0.125 seconds in duration, and pin 4 of the counter 30B carries a pulse of approximately 0.25 seconds in duration. The 0.125 second pulse and the 0.25 second pulse are connected to input pins 12 and 13 of NAND gate 30C respectively. The output of the gate 30C at pin 11 is therefore a 0.1 second pulse occurring approximately every 0.5 seconds. This output at pin is connected to input pins 9 and 10 of NAND gate 30D which serves as an inverter.

The output of the NAND gate 30D at pin 8, i.e., the 0.125 second pulse, is connected to pin 11 of the counter 22A via line 108 to reset the counter. It is also connected to the clock input pin 11 of the latch 24, via line 110. Therefore, when the 0.125 pulse occurs, the latch 24 accepts the count of the counter 22A via parallel input lines 112a-h. The output of the latch 24 at pins 2, 5, 6, 9 12 15 16 and 19 appears on lines 114a-h respectively, which are connected to pins 1-7 and 23, respectively, of the PAL 26. Latch 24 can be a standard octal d-type flip flop with reset, part number 74/HCT273, as manufactured by Signetics Co., National Semiconductor Corp., Texas Instruments, and others.

The counter 22A counts the input pulses between reset pulses for approximately a 0.4 second time delay period. Although in the preferred embodiment the input pulses are counted for 0.4 seconds other durations can be used. For example, the pulses can be counted for 0.2 seconds and added to the previous 0.2 second count to operate with less delay between the start of a count and the output of the signal from the PAL 26 which represents the count. The time delay is chosen to coordinate the sound produced with the speed of movement of the radiation probe by the surgeon. The time delay may be shortened for faster movement of the probe, i.e., for those who tend to move the probe rapidly.

Lines 104a-e from the divider 30A carrying the 4 KHz, 2 KHz, 1 KHz, 5 KHz and 25 KHz signals, respectively, are connected to pins 14, 13, 11, 10, and 16, respectively, of the PAL 26. In addition, the divider 30B outputs at pins 3 and 5 are connected to pins 8 and 9 of the PAL 26 via lines 106a and 106b. These signals provide repetition rates of 8 and 16 Hz for the frequencies provided by the frequency divider 30A to the PAL 26 and are transmitted to the speaker 12.

As stated previously, the PAL 26 compares the incoming count to an internal look-up table establishing the various count ranges described earlier and chooses the appropriate count range for the incoming counts. Preprogrammed into the PAL 26 is an established predetermined frequency and repetition rate for each count range for synthesizing the audible output signals.

The PAL 26 can be a standard 20V10 circuit, such as provided by the Lattice Semiconductor Corporation. It is programmed using a standard ABEL program provided by the Data I/O Corp. of Redmond, Washington.

As can be seen in Table I, the count ranges have been further subdivided into sets of 5 sub-ranges, each comprising 3 count ranges. A particular tone of frequency is assigned to each sub-range. Thus, for counts 1-3, an audio output signal of 250 Hz with a slow repetition rate, e.g., 8 times a second, is generated. As the count increases into the 4-7 range, the 250 Hz signal is generated with a medium repetition rate, e.g. 16 times a second. Further increase of the count into the 8-11 range will result in an output signal which is a continuous 250 Hz tone. Thus, as the count progressively increases, the frequency of the output signal increases progressively to 500 Hz, 1000 Hz, 2000 Hz, and 4000 Hz, and each of these tones are generated first at a slow repetition rate, then a medium repetition rate, then a continuous repetition rate. As mentioned earlier, Table I is exemplary, and other frequencies and repetition rates may be used. In addition, other parameters may be used, such as intensity of tone and period of pulse, which can be varied to indicate changes of input count. A continuous tone is considered to have period approaching infinity.

The repetition rates and tones are chosen so that a change in tone or a change in repetition rate is easily discernable by the user. In place of tones of individual frequencies, musical voices with harmonics which are pleasing to the ear and which can be tolerated for extended periods of time, can be used.

Each of the ranges established has a mean value which is chosen to be statistically different than the mean value of the preceding or succeeding count range. Thus, each of the ranges may be chosen so that its mean is 1, 2, or 3 standard deviations different from the means of the succeeding and preceding ranges. For 1, 2, or 3 standard deviations, the probability that the received signal in a particular range differs from the received signal of other ranges is 67%, 95% and 99.0% respectively. Therefore, the surgeon, in using the apparatus of the instant invention, is assured that there is a high probability that any changes in audible signal which occurs as the probe is moved over various parts of the patient's body represents a statistically valid change in radiation levels.

It is possible that at boundaries between count ranges, a change of 1 or 2 counts can cause a change in output frequency, causing an audible warbling effect. This can be addressed by inserting logic to prevent a change in output frequency unless the count has changed by a predetermined amount or percentage.

The visual display 34 is optional and comprises a series of L.E.D.'s (light emitting diodes), which are arranged horizontally or vertically, as is commonly used for tuning of conventional AM/FM tuners. As the count increases, successive L.E.D.'s fire indicating to the surgeon levels of detected radiation. The L.E.D. input on lines 117 is connected to suitable terminals of the PAL 26, which can be easily determined by those skilled in the art.

As should thus be appreciated, an apparatus and method has been disclosed which provides users of radiation probes with statistically valid information relating to changes in counts per second of detected radiation. A series of audible signals which are easily discernable from each other, indicate to the user, as the position of the radiation probe is changed that meaningful changes in radiation counts per second are occurring. Although the preferred embodiment relates to the synthesis of audio signals from radiation detector outputs, the invention is equally applicable to the retrieval of target data in a high noise background from other sources, such as CAT scan representations, Infra-red photographic representations, electrical signals of forms other than pulse inputs from radiation detectors, etc.

Without further elaboration, the foregoing will so fully illustrate our invention that others may, by applying current or future knowledge, adapt the same for use under various conditions of service.

What is claimed is:

1. Signalling apparatus for use with an examination system, said examination system being arranged for examining an object to provide electrical input signals to said signalling apparatus, said input signals having a range of repetition rates which are a function of predetermined characteristics of said object, said signalling apparatus comprising means for processing said input signal, said processing means processing all input signals without deriving any squelch level, said processing means comprising: counting means, rate establishing means, and responsive means, said counting means counting said electrical input signals from said examination system, said rate establishing means establishing a plurality of respective count ranges, said plurality of count ranges being arranged in numerical sequence, with each one of said plurality of count ranges having a mean value which is a predetermined value different from the mean value of numerically adjacent count ranges, said plurality of count ranges comprising counts covering an entire range of said repetition rates of said electrical input signals, said responsive means being responsive to said counting means and coupled to said rate establishing means for producing an output signal for each of said count ranges representative of said predetermined characteristic of said object, each of said output signals being readily discriminable from every other of said output signals by a human being.

2. The apparatus of claim 1 wherein said humanly discriminable output signals comprise audible signals.

3. The apparatus of claim 2 wherein said examination system produces output signals representative of radiation emanating from an object.

4. The apparatus of claim 3 wherein said system is arranged for finding tumors tagged with a radiopharmaceutical, whereupon said electrical output signals are indicative of the radiation emanating from said object and which is detected by said examining system.

5. The apparatus of claim 4 wherein each of said count ranges comprises plural sub-ranges and wherein said output signal for each of said sub-ranges of each count range comprises a constant characteristic and a variable characteristic.

6. The apparatus of claim 5 wherein said constant characteristic comprises a respective predetermined tone for each of said count ranges and wherein said variable characteristic comprises at least two repetition rates of said tone.

7. The apparatus of claim 5 wherein said constant characteristic comprises a respective predetermined tone for each of said count ranges and wherein said variable characteristic comprises at least two time durations of said tone.

8. The apparatus of claim 5 wherein said constant characteristic comprises a respective predetermined tone for each of said count ranges and wherein said variable characteristic comprises at least two intensities of said tone.

9. The apparatus of claim 5 wherein said constant characteristic comprises a predetermined musical voice for each of said count ranges and wherein said variable characteristic comprises at least two variations of said musical voice.

10. The apparatus of claim 9 wherein said at least two variations of said musical voice comprises at least two repetition rates of said musical voice.

11. The apparatus of claim 9 wherein said at least two variations of said musical voice comprises at least two time durations of said musical voice.

12. The apparatus of claim 9 wherein said at least two variations of said musical voice comprises at least two intensities of said musical voice.

13. The apparatus of claim 1 wherein said electrical output signals comprises electrical pulses and said counting means comprises means for counting said pulses for a predetermined time period.

14. The apparatus of claim 13 wherein said humanly discriminable output signals comprise audible signals.

15. The apparatus of claim 14 wherein said examination system produces output signals representative of radiation emanating from an object.

16. The apparatus of claim 15 wherein said system is arranged for finding tumors tagged with a radiopharmaceutical, whereupon said electrical output signals are indicative of the radiation emanating from said object and which is detected by said examining system.

17. The apparatus of claim 16 wherein each of said count ranges comprises plural sub-ranges and wherein said output signal for each of said sub-ranges of each count range comprises a constant characteristic and a variable characteristic.

18. The apparatus of claim 17 wherein said constant characteristic comprises a respective predetermined tone for each of said count ranges and wherein said variable characteristic comprises at least two repetition rates of said tone.

19. The apparatus of claim 17 wherein said constant characteristic comprises a respective predetermined tone for each of said count ranges and wherein said variable characteristic comprises at least two time durations of said tone.

20. The apparatus of claim 17 wherein said constant characteristic comprises a respective predetermined tone for each of said count ranges and wherein said variable characteristic comprises at least two intensities of said tone.

21. The apparatus of claim 17 wherein said constant characteristic comprises a predetermined musical voice for each of said count ranges and wherein said variable characteristic comprises at least two variations of said musical voice.

22. The apparatus of claim 21 wherein said at least two variations of said musical voice comprise at least two repetition rates of said musical voice.

23. The apparatus of claim 21 wherein said at least two variations of said musical voice comprise at least two time durations of said musical voice.

24. The apparatus of claim 21 wherein said at least two variations of said musical voice comprise at least two intensities of said musical voice.

25. The apparatus of claim 13 wherein said predetermined time period is approximately 0.4 second.

26. The apparatus of claim 13 wherein said predetermined time period is approximately 0.2 sec and the count of the previous 0.2 sec period is added to the count of the pulses obtained during said predetermined time period.

27. The apparatus of claim 13 wherein said responsive means comprises means to compare each count of said pulses taken for said predetermined time period to each of said count ranges and means to select the count ranges in which said each of said counts is included.

28. The apparatus of claim 27 wherein said responsive means produces a discriminably different output signal for each of said selected count ranges.

29. The apparatus of claim 28 wherein said discriminable output signals comprise audible signals.

30. The apparatus of claim 29 wherein said examination system provides output signals representative of radiation emanating from an object.

31. The apparatus of claim 30 wherein said system is arranged for finding tumors tagged with a radiopharmaceutical, whereupon said electrical output signals are indicative of the radiation emanating from said object and which is detected by said examining system.

32. The apparatus of claim 13 wherein each of said count ranges comprises plural sub-ranges.

33. The apparatus of claim 32 wherein said responsive means comprises means to compare each of said counts for a predetermined count period to each of said sub-ranges and means to select the sub-range in which each of said counts is included.

34. The apparatus of claim 33 wherein said responsive means produces a discriminably different output signal for each of said selected sub-ranges.

35. The apparatus of claim 34 wherein said humanly discriminable output signals comprise audible signals.

36. The apparatus of claim 35 wherein said examination system produces output signals representative of radiation emanating from an object.

37. The apparatus of claim 36 wherein said system is arranged for finding tumors tagged with a radiopharmaceutical, whereupon said electrical output signals are indicative of the radiation emanating from said object and which is detected by said examining system.

38. The apparatus of claim 1 wherein the said predetermined value is one to three standard deviations.

39. The apparatus of claim 38 wherein said discriminable output signals comprise audible signals.

40. The apparatus of claim 39 wherein said examination system produces output signals representative of radiation emanating from an object.

41. The apparatus of claim 40 wherein said system is arranged for finding tumors tagged with a radiopharmaceutical, whereupon said electrical output signals are indicative of the radiation emanating from said object and which is detected by said examining system.

42. The apparatus of claim 1 wherein each of said count ranges comprises plural sub-ranges, each of said sub-ranges being arranged in numerical sequence within each of said count ranges and each of said sub-ranges having a mean value which is a predetermined value different from the mean of the preceding sub-range and the succeeding sub-range.

43. The apparatus of claim 42 wherein said predetermined value is one to three standard deviations.

44. The apparatus of claim 43 wherein said humanly discriminable output signals comprise audible signals.

45. The apparatus of claim 44 wherein said examination system produces output signals representative of radiation emanating from an object.

46. The apparatus of claim 45 wherein said system is arranged for finding tumors tagged with a radiopharmaceutical, whereupon said electrical output signals are indicative of the radiation emanating from said object and which is detected by said examining system.

47. The apparatus of claim 1 wherein said apparatus further comprises display means responsive to said output signals.

48. A method for locating radiation emitting sources in living beings comprising the steps of:
(a) placing a radiation detection probe, which generates a series of electrical pulses over a range of repetition rates over part of the body of said living being;
(b) processing said electrical pulses without deriving any squelch level, said processing comprising the steps of:
(1) counting the pulses detected by said probe for a predetermined amount of time;
(2) establishing a set of count ranges which include a full range of said repetition rates;
(3) establishing a signal for each of said count ranges which is discriminable from the signal generated for every other of said count ranges;
(4) comparing each of said count ranges to the count detected for said predetermined amount of time;
(5) selecting the count range in which said detected count is included; and
(6) producing an output signal which comprises said established signal for the count range which has been selected.

49. The method of claim 48 further comprising the step of transducing said output signal to produce an audible signal.

50. The method of claim 49 further comprising the steps of establishing a respective frequency and a respective repetition rate for each of said established signals.

51. The method of claim 49 further comprising the steps of establishing a particular musical voice and repetition rate for each of said established signals.

52. The method of claim 48 further comprising the step of generating a display representative of said output signal.

53. A method for locating radiation emitting sources in a living being comprising the steps of:
 (a) placing a radiation detection probe, which generates a series of electrical pulses over a range of repetition rates, over part of the body of said living being;
 (b) processing said electrical pulses without deriving any squelch level, said processing comprising the steps of:
  (1) counting the pulses detected by said probe for a predetermined amount of time;
  (2) establishing a set of count ranges which include a full range of said repetition rates;
  (3) establishing a plurality of sub-ranges for each of said count ranges;
  (4) establishing a signal for each of said sub-ranges which is discriminable from the signal generated for every other of said sub-ranges;
  (5) comparing each of said sub-ranges to the count detected for said predetermined amount of time;
  (6) selecting the sub-range in which said detected count is included; and
  (7) producing an output signal which comprises said established signal for the sub-range which has been selected.

54. The method of claim 53 further comprising the step of transducing said output signals to produce an audible signal.

55. The method of claim 54 further comprising the step of generating a display representative of said output signal.

56. The method of claim 55 further comprising the steps of establishing a respective frequency and repetition rate for each of said sub-ranges.

57. The method of claim 55 further comprising the step of establishing a particular musical voice and repetition rate for each of said sub-ranges.

* * * * *